(12) United States Patent
Weiss

(10) Patent No.: US 6,733,131 B1
(45) Date of Patent: *May 11, 2004

(54) EYE SELF-TEST DEVICE

(76) Inventor: Jeffrey N. Weiss, 7600 Ventura La., Parkland, FL (US) 33067

( * ) Notice: Subject to any disclaimer, the term of this patent is extended or adjusted under 35 U.S.C. 154(b) by 0 days.

This patent is subject to a terminal disclaimer.

(21) Appl. No.: 09/784,370

(22) Filed: Feb. 15, 2001

Related U.S. Application Data

(63) Continuation-in-part of application No. 09/566,310, filed on May 8, 2000, which is a continuation of application No. 09/245,481, filed on Feb. 5, 1999, now Pat. No. 6,068,378.
(60) Provisional application No. 60/110,736, filed on Dec. 3, 1998.

(51) Int. Cl.7 .................................................. A61B 3/02
(52) U.S. Cl. ..................................................... 351/223
(58) Field of Search ................................ 351/200, 222, 351/223, 224, 227, 239, 243, 177, 246; 248/309.4; 368/29, 41, 10; 40/107; 434/238; 348/818; 345/700, 701, 854; 482/8; 340/309.3

(56) References Cited

U.S. PATENT DOCUMENTS

| | | | | |
|---|---|---|---|---|
| 3,883,234 A | * | 5/1975 | Lynn et al. | 351/224 |
| 4,162,610 A | * | 7/1979 | Levine | 368/41 |
| 4,783,922 A | * | 11/1988 | Moore | 40/107 |
| 5,056,909 A | * | 10/1991 | Brown et al. | 351/177 |
| 5,565,934 A | * | 10/1996 | Boudreau et al. | 348/818 |
| 5,646,710 A | * | 7/1997 | Caskey | 351/223 |
| 5,691,932 A | * | 11/1997 | Reiner et al. | 368/10 |
| 5,861,797 A | * | 1/1999 | Becker | 340/309.3 |
| 5,890,997 A | * | 4/1999 | Roth | 482/8 |
| 5,946,075 A | * | 8/1999 | Horn | 351/246 |
| 6,042,383 A | * | 3/2000 | Herron | 434/238 |
| 6,310,634 B1 | * | 10/2001 | Bobnar et al. | 345/854 |
| 6,342,901 B1 | * | 1/2002 | Adler et al. | 345/700 |

* cited by examiner

*Primary Examiner*—George Manuel
(74) *Attorney, Agent, or Firm*—Malin, Haley & DiMaggio, P.A.

(57) ABSTRACT

The novel design of the eye self-test device increases patient compliance by reminding the patient to self-test and allows the patient's doctor to monitor compliance with the testing regimen. The data may be recorded and the patient notified if a change in vision necessitates examination by the doctor. The test is robustly manufactured to withstand breakage and is lightweight and portable. Its preferred method of attachment is such that it is capable of adhering to any vertically visible surfaces such that the conspicuous location of the test should encourage an improvement in testing compliance. Patient information, including instructions for testing and the doctor's name and telephone number for contacting in case of emergency may be provided internal or external to the device. In an alternative embodiment, an event reminder is provided which can also include an eye-self test.

17 Claims, 5 Drawing Sheets

EYE SELF-TEST DEVICE

CROSS-REFERENCE TO RELATED APPLICATIONS

This application is a continuation-in-part of application Ser. No. 09/566,310, filed May 8, 2000, which is a continuation of application Ser. No. 09/245,481, filed Feb. 5, 1999, now U.S. Pat. No. 6,068,378, issued May 30, 2000, which claims the benefit of Provisional Application Serial No. 60/110,736, filed Dec. 3, 1998.

STATEMENT REGARDING FEDERALLY SPONSORED RESEARCH OR DEVELOPMENT

N/A

BACKGROUND OF THE INVENTION

1. Field of the Invention

This invention relates to medical diagnostic methods, and, in particular, to a method for improving the compliance and reliability of patient self-testing the central field of vision. The device is set for test recording in one day or another interval and notifies the patient to self-test if it is not activated within the preset interval. A play-back counter or tracker indicates whether the patient has been complying with the testing schedule. The patient may be notified when a predetermined change from the normal test or baseline test is detected and is instructed to contact their physician.

2. Description of Related Art

The macula is a small area within the retina of the eye that allows us to see small details clearly. If a person loses macula function they experience a blur or a blank spot in the center of their vision. There are many diseases that affect the macula. The early detection of macular changes may result in successful treatment that may prevent or delay the loss of vision. Unfortunately, once the patient notices the loss of vision it may already be too late to treat the condition and prevent or reverse the loss of vision.

In order to monitor the health of the macula, patients are frequently given a grid of lines with a central spot. They are instructed to self-test their vision with the grid at a set interval, generally once a day or every other day and contact their eye doctor if they notice a bending or absence of the lines or change in vision. The manner in which the test is altered may also provide clues to diagnosis. Unfortunately, many patients forget to use the test and discard or lose it over the course of time. As a result, many patients that might have presented to their doctor early enough to have their vision saved lose their central vision unnecessarily. The early detection of a change in vision will become even more important as newer treatments for macular diseases become available.

It is therefore, to the effective resolution of the aforementioned problems and shortcomings that the present invention is directed.

Accordingly, it is an object of this invention to provide an eye test where the patient can determine changes from normal.

It is another object of this invention to provide, by its configuration and method of attachment, a small, lightweight and portable device with stable adherence to a surface such that the test may be placed in a location that is conspicuously visible to the patient and will not be lost or accidentally discarded. The device is surrounded by a hard case to minimize breakage.

It is still another object of this invention to provide a timer that is preset for the patient's self-testing. If the patient does not self-test within the designated period of time, a sound or light is activated at preset times and duration to remind the patient to self-test.

It is yet another object of this invention to provide the patient's doctor's name, address and telephone number such that this information is readily available in case of emergency.

It is a further object of this invention to provide a long-lasting internal battery or rechargeable power supply for the device to obviate the need for frequent battery changes.

It is a further object of this invention to provide a device that records patient compliance with the preset testing frequency and that may be examined by the eye doctor to determine patient compliance.

It is yet another object of this invention to provide a device that notifies the patient when a preset deviation from normal occurs. The notification would encourage the patient to contact the eye doctor for examination.

It is a further object of this invention to provide a device that contains a transmitter or a port for attachment to a telephone line for monitoring by a monitoring station, an intelligent docking station or to a computer that would alert the patient when a significant change in the test occurred and would instruct the patient to promptly contact their eye doctor.

BRIEF SUMMARY OF THE INVENTION

The foregoing objects are achieved and the foregoing problems are solved in one illustrative embodiment of the invention in which a grid is attached to a case containing electronics such that once the device is activated the patient self-tests according to a preset testing frequency. The device is lightweight and contains magnets and/or an adhesive for easy attachment to a vertically conspicuous location in which the test would be prominently displayed. The case contains a place for the eye doctor's business card or a label containing the eye doctors name and contact information or other information. If the patient does not self-test, a sound or light is activated at preset times and for a preset interval to encourage the patient to self-test. The eye doctor may play-back the number of patient self-tests to determine the patient's compliance. The patient may draw the deviations from normal on the grid and when a preset deviation from normal occurs the patient would be notified to promptly contact the doctor. The notification may consist of a sound or light generated by the device or external notification by a monitoring station, intelligent docking station, computer, eye doctor or other source.

It is estimated that in the preferred embodiment, the squares on the grid can be 4 mm in size. The grid and central fixation spot can be black on a white background and the grid test can be approximately 8 cm by 8 cm in size. The single grid test can be attached to a case approximately 9 cm in width and 10 cm in length. The test is to be performed with one eye at a time under a moderate light intensity while wearing the correct refraction for reading at approximately a 14 inch distance. However, these dimensions and criteria are not considered limiting and other ranges and values are considered within the scope of this invention.

The illustrated embodiment describes a device for detecting irregularities in the central 20 degrees of vision. It will be apparent to those skilled in the art that a similar patient compliance and monitoring methodology may be used for other self-testing devices including reading vision, glare or color vision.

In a first embodiment of the present invention the grid is made of paper, plastic or another material that may or may not record images. In a second embodiment the chart is displayed on a screen. In a third embodiment a port is provided for computer and/or telephone access. In a fourth embodiment one grid is displayed for one eye and a second is displayed for the second eye. The patient presses one button when self-testing. In a fifth embodiment the patient presses a button for performing the test with one eye and a second button for performing the test on the second eye.

In a sixth embodiment of the present invention the self-test includes one button and a timer. The patient, doctor or other person presses the button to program the timer duration, i.e., one, two, three, etc. days. When the patient presses the button the timer is started. An alarm, light emitting diode (LED), or other notification device will activate if the patient does not press the button in the preset time interval. As an example, the notification device may be set to activate every 30 minutes for 2 hours if the button is not pressed. Alternatively, an alarm may activate periodically but an LED may continue blinking if the button is not depressed. The notification device activation times and duration may be preset. Once the patient presses the button the timing sequence is reset. The grid may be imprinted on the device or alternatively placed within a transparent pocket within the grid. Other information, such as instructions or advertising may be imprinted on the device or placed within the transparent pocket. It is also apparent that the grid or transparent pocket may have a writable surface to allow the patient to record any deviations from the expected.

In a seventh embodiment of the present invention the self-test incorporates a multitude of lights such as LEDs vertically arranged under the grid test, an alarm and timer. Next to each LED is a button, a number ranging from 1 to, for example, 4 which refers to the daily frequency of medication usage (i.e., 1 for once a day medication, 2 for twice a day medication, etc.) and an erasable strip where the names of the medications may be written. Alternatively the area may be used to place an adhesive strip containing the names of the medications. Each button sets the timer which activates the LED/alarm to inform the patient when it is time to take their medication. Alternatively, one button may be used to program the LED and alarm associated with each line. In another embodiment the patient may press a button next to the medication the number of times per day that they will take the medication, i.e., by pressing the button three times the notification device will be activated every 8 hours. It will be apparent to those skilled in the art that any combination of LEDs and/or buttons and various programming schemes may be used to perform the function of reminding a person when to take a medication.

In an eighth embodiment of the present invention each line also has a digital readout that indicates the number of medication doses that have already been taken and/or yet to be taken within a time period. The presumed time period is 24 hours but other periods may also be programmed. The number in the digital readout may flash when the next dose of medication is to be taken.

In a ninth embodiment of the present invention the individual light/alarm associated with each line may be programmed by the patient, doctor or pharmacist to activate at pre-determined times.

In a tenth embodiment of the present invention the entire device may be used as a medication reminder or alternatively, a reminder for other events. It is apparent, that the size of the device is not a limiting factor, and that sizes larger or smaller (allowing portability) are possible.

In accordance with these and other objects which will become apparent hereinafter, the instant invention will now be described with particular reference to the accompanying drawings.

DETAILED DESCRIPTION OF THE INVENTION

Figures 1A, 1B:
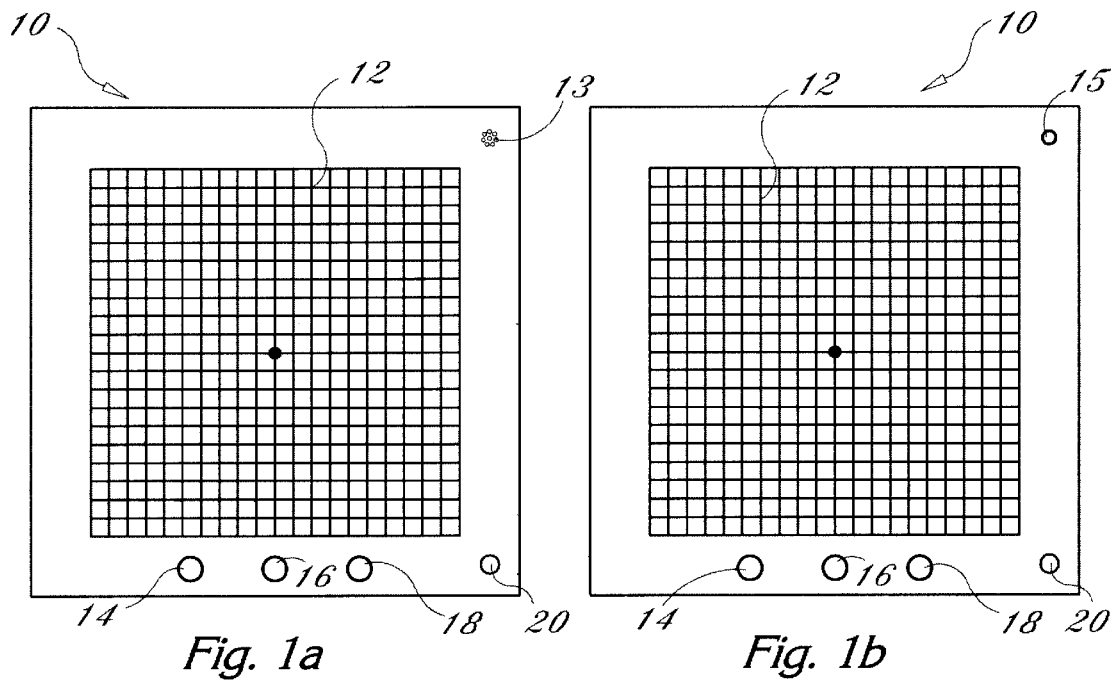
FIG. 1a is a front view of the present invention, and also illustrates an optional speaker member.
FIG. 1b is a front view of the present invention, and also illustrates an optional lighting element.
Figure 2:
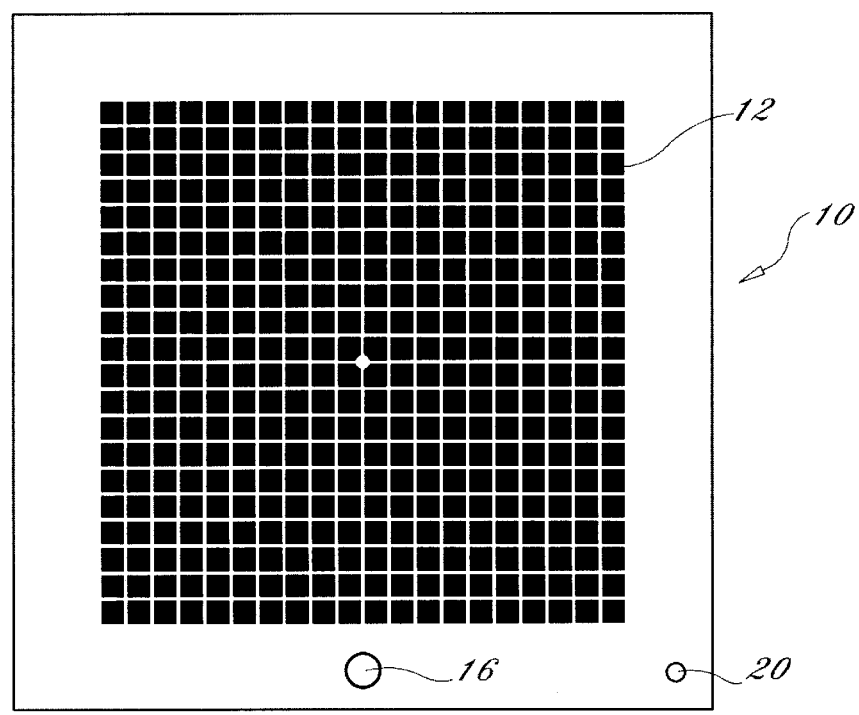
FIG. 2 is a front view of the present invention, illustrating an alternative background for the chart or grid.

As seen in FIG. 1a or 1b a first embodiment of the eye self test in accordance with the present invention is shown and generally designated test 10. Eye self test 10 includes a grid or chart 12, having a plurality of boxes and a central fixation spot. The lines and fixation spot may be dark on a light background (FIG. 1a or 1b) or alternatively light on a dark background (FIG. 2). Eye self test 10, including grid 12 may be made from a material that may or may not be written on, such as paper, plastic, and other conventional materials. If the surface is writable then the material may allow permanent recording or erasing. A recording instrument, such as a conventional pen or pencil, may be included.

Eye test 10 provides an alarm to the user, such as audio indicator (speaker) 13 (FIG. 1a) and/or visual indicator (light) 15 (FIG. 1b). The alarm indicates that it is time to administer a self-examination. In order to conserve battery life the device is first activated by pressing a button. Alternatively, the battery may be rechargeable. The device is then programmed for test recording in one, two or three day or another interval, preferably by pressing one of the buttons 14, 16 or 18 which are in communication with the circuitry or microprocessor of eye test 10. Alternatively, a three position switch 62 can be provided and is in communication with the circuitry or microprocessor of eye test 10. The user merely sets switch 62 to the desired interval. Switch 62 can be provided at the back of eye test 10 (FIG. 4) or any other location on eye test 10. Other intervals, not shown, can be provided and are considered within the scope of the invention. Additionally, a single button, such as button 16 (FIG. 2), can be used, with the user pressing on the button for different time periods or a specific amount of successive times to indicate which time interval is desired.

When performing the test, the patient presses a button 20. The device acknowledges the self-test with a sound or light or other means and increases the test taken count. An additional button push within the same testing interval is not recorded by the device. If the test is not taken within the preset testing interval, the device will notify the patient through a sound, light, telephone call or other means.

In one embodiment, the device will activate a beeping sound five times at five second intervals at noon, 3 pm, 5 pm and at 7 pm on the missed day. By depressing a button, such as button 20, in a known fashion and in a known frequency and duration, the eye doctor will, by light, sound, a counter or tracker, or other determination devices, both internal and external to the device, determine the compliance of the patient to the self-testing schedule.

Figure 3:
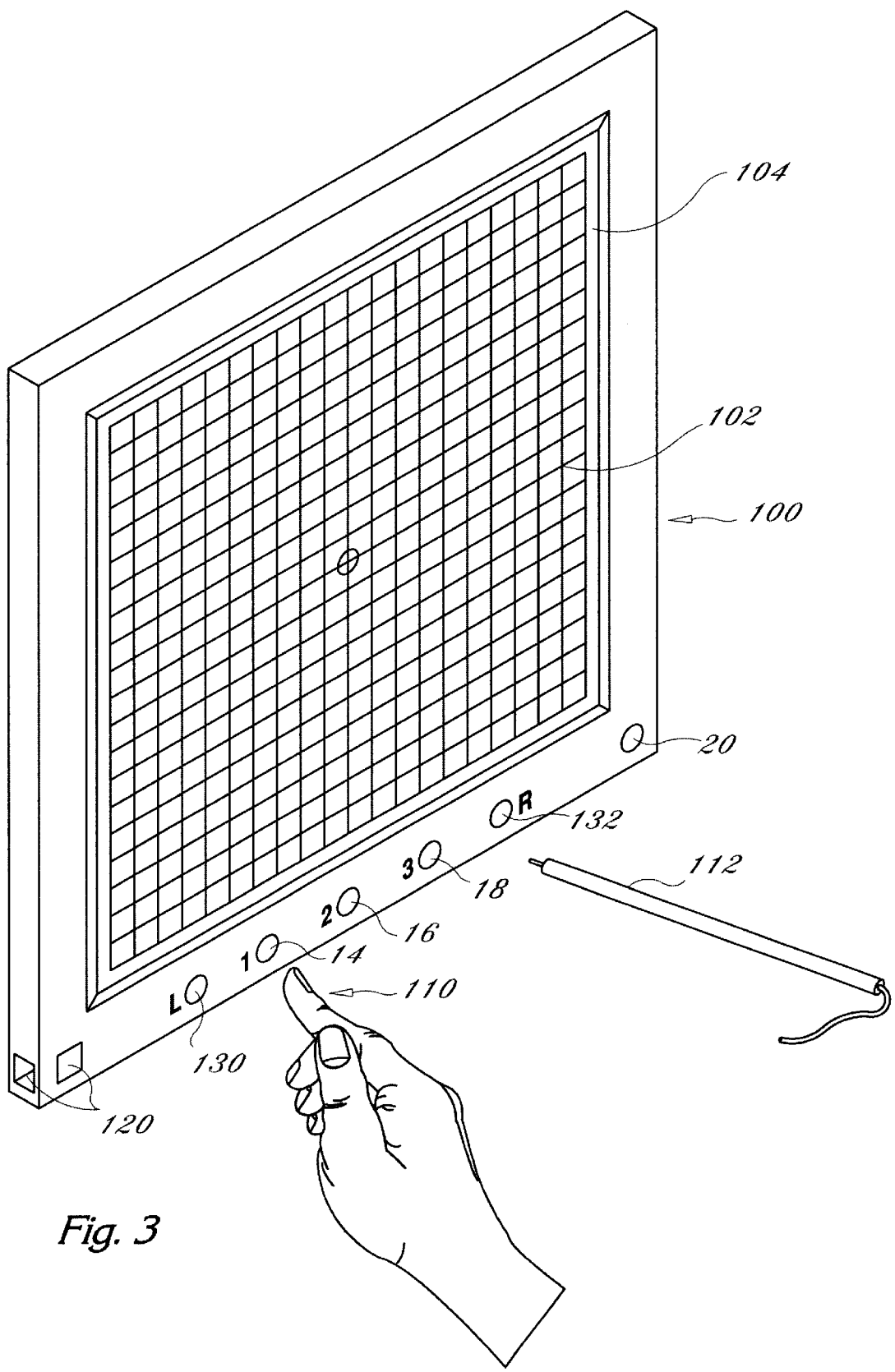
FIG. 3 is a perspective view of an alternative embodiment of the present invention in which the chart or grid is displayed on a screen.

An alternative embodiment of the present invention is generally designed test 100 and includes a similar grid 102 which is displayed on a screen member 104 (FIG. 3). The patient may record changes on the grid using his or her finger 110 or alternatively an included conventional recording marker 112 and the initial changes from normal are recorded. Significant variations in the test recording from normal or from the baseline test, as determined by internal software would notify the patient that the eye doctor should be contacted. Alternatively, a conventional transmitter may be provided, with test 100, such that external analysis of the test recording and notification of the patient may be provided by a computer, monitoring station, external docking station, eye doctor, or other source.

A conventional computer port and/or conventional telephone port 120 can be provided with test 10 or 100. If a significant variation in the test recording is determined by internal or external software, then the patient may be notified by the doctor, a monitoring company, or other means.

Additionally, a resettable audible, visual, digital and/or mechanical indicator, not shown, can be provided and will be in communication with the test taking counter or tracker of eye test 10 or 100. The counter or tracker, or similar device, records patient compliance with the preset testing frequency and can be examined by the eye doctor to determine patient compliance. The indicator would quickly inform the doctor of the amount of times the patient has administered the test since the last time the doctor reviewed eye test 10 or 100. A button or other conventional mechanism could be provided to reset the indicator back to zero.

Two separate tests 10 or 100, one for the left eye (FIG. 1*a* or 2), and one for the right eye (FIG. 1*b* or 2), can also be utilized and is considered within the scope of the present invention. The patient may push one button, when self-testing both eyes. In another embodiment (FIG. 3), one computerized grid is provided, using conventional technology. In this embodiment, information for each eye is programmed. When the patient pushes left eye button 130, information for the patient's left eye is retrieved by the computer, to allow the user to test his or her left eye. When the patient pushes right eye button 132, information for the patient's right eye is retrieved by the computer, to allow the user to test his or her right eye.

Figure 4:
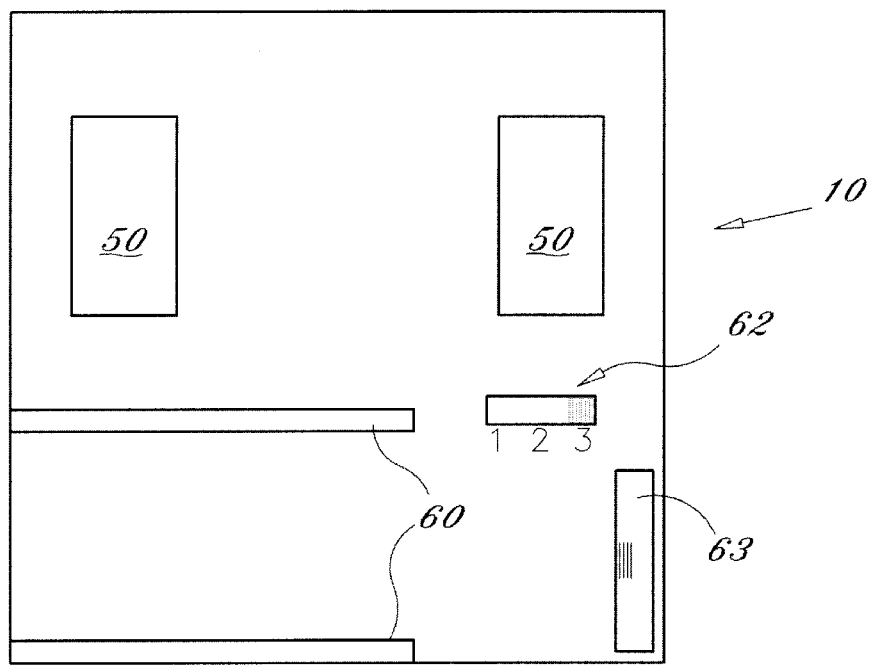
FIG. 4 is a back view of the present invention.
Figure 5:
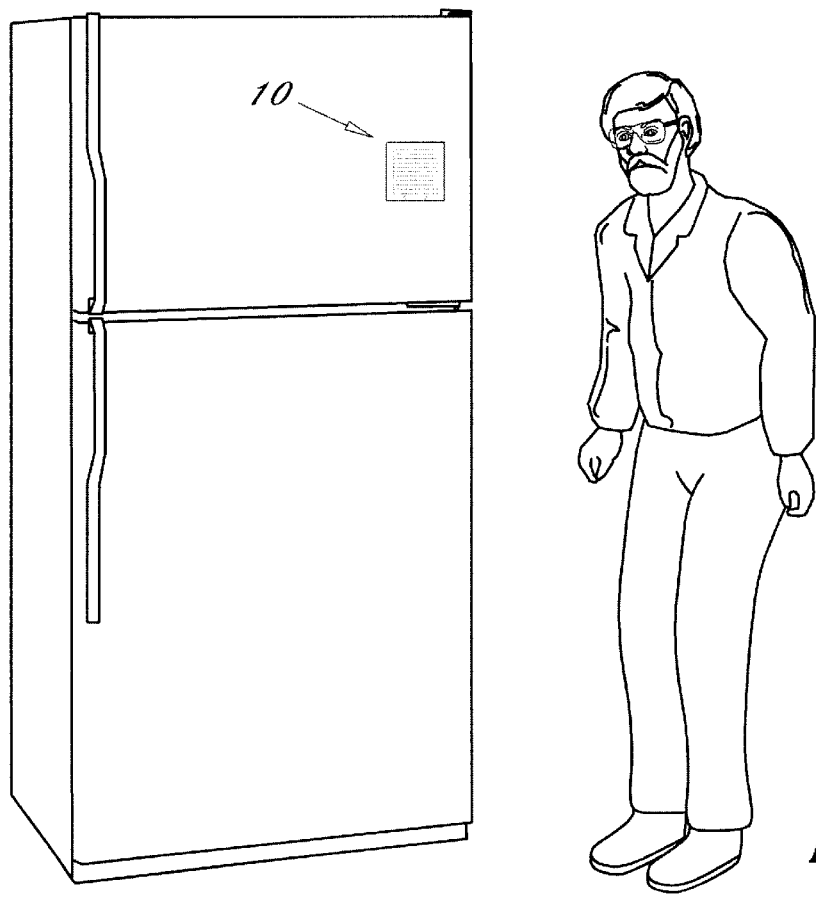
FIG. 5 is a perspective view of the present invention illustrating an individual using the present invention which is attached to the outer surface of a conventional refrigerator.

FIG. 4 illustrates the back surface of either eye test 10 or 100. One or more magnets 50 and/or another permanent or removable adhesive or attachment device is used to attach test 10 or 100 to a visible surface. FIG. 4 also illustrates battery compartment 63 which is provided when a battery (not shown) is used to power device 10 or 100. Alternatively, and in lieu of a battery, a rechargeable power supply can be used and is also considered within the scope of the invention. The lightweight nature of the device 10 or 100 allows it to be attached to a vertical surface. Retaining ledges 60 can be provided for storing a doctor's card, instructions for performing the test and/or other relevant information. FIG. 5 illustrates an individual using test 10 or 100 which is attached to the outer surface of a conventional refrigerator.

It is apparent to those skilled in the art that if the recording of the patient's test changes are desired, then one preferred embodiment is to use a test containing two grids. Alternatively, a computerized screen may display within a single grid size format the patient's recorded responses from each eye, and other information including a normal test, the instruction for performing the test and the doctor's name, address and telephone number for contacting in case of emergency. Though the invention is preferably used with a vertical surface, it should be recognized that the invention can also be used on a horizontal or diagonal surface and such uses are also within the scope of the invention.

Figure 6:
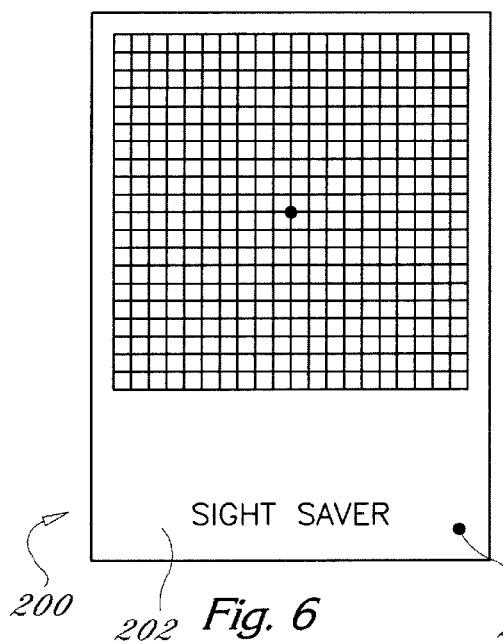
FIG. 6. Illustrates a front view of the sixth embodiment of the eye self-test device which contains a patient activated timer. Space can be provided for advertising.

FIG. 6 illustrates a sixth embodiment of the eyes self-test device (200) in which the button (201) is depressed to set the timer duration. As an example, if the button is held for 4 seconds an alarm and/or LED activates twice to indicate a 24 hour duration. If the button is depressed for 7 seconds the notification device will activate three times indicating a three day period, 10 seconds will indicate a 7 day period, etc. The pressing of the button activates a notification device to inform the user that the action has been acknowledged and activates the timer. If the button is not depressed within the preset time interval an alarm, beeping sound, light, or combination of sound and light activates for a preset time and duration. As an example, an LED may remain blinking and an audible alarm may activate for 10 seconds every hour for three hours until the button is again depressed. The front surface of the device contains room for advertising or other messages (202). The grid may be imprinted on the device or a transparent pocket may be provided such that a folded item containing i.e., grids in different colors, instructions for use, advertising, etc. may be placed within the pocket. The back surface of the case contains adhesive devices such as magnets and adhesive tape. The front, back, or front pocket of the device may also include the instructions for the use of the self-test as well as the name, address and telephone number of the patients eye or another doctor. Programming capability or a counter may be incorporated in the device such that the degree of patient compliance in performing the test may be ascertained.

Figure 7:
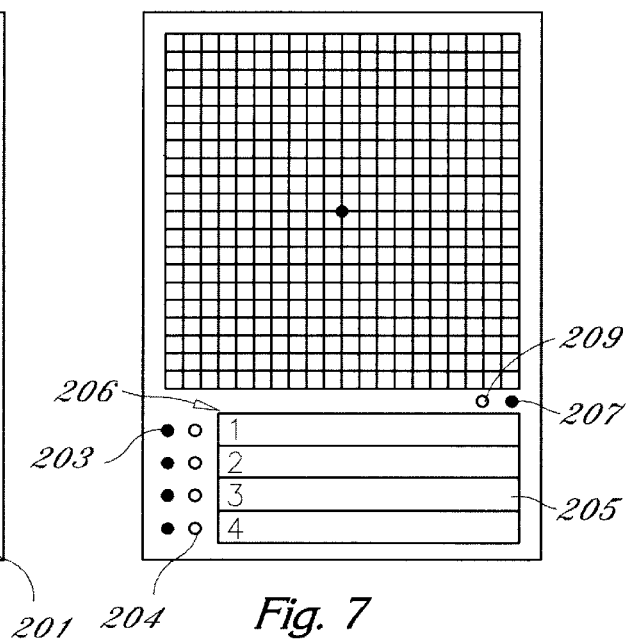
FIG. 7. Illustrates a front view of the seventh embodiment of the eye self-test device in which an additional area is provided as a reminder for patients to take their medications.

FIG. 7 illustrates a seventh embodiment of the eye self-test device. There is a button (207) and LED (209) associated with the grid and there are 2 vertical lines consisting of buttons (203) and LEDs (204) next to a horizontal line where the name or names of medications may be written on an erasable surface (205).

Alternatively, the name or names of the medications may be written or typed on an adhesive material and placed in the horizontal area. The first horizontal line corresponds with a "1" (206), symbolizing a medication taken once a day, the second horizontal line with a "2", symbolizing a medication taken twice a day, the third horizontal line with a "3", symbolizing a medication taken three times a day and the fourth line with a "4", symbolizing a medication taken four times a day. It is apparent that the number of lines and the associated symbols are not limiting factors and that more or less lines and other symbols representing the frequency of medication usage may also be used. The grid may or may not be associated with a separate button (207) for the grid timer if so desired. Alternatively, one button for programming the frequency of grid testing and of medication usage may be provided, such that each horizontal line is not limited in the frequency of medication usage. The patient would press this same button when performing the grid test and when taking the medication in response to the flashing LED next to the particular medication to be taken.

In the present example (FIG. 7), the medication reminder is activated when the patient depresses the button next to the medication to be taken. If the button for a medication taken once a day is depressed then the alarm and/or LED or another notification means will be activated 24 hours later. If the person does not depress the button at that time then the alarm will sound and/or LED will activate every hour on the hour for 20 seconds for 5 hours or for another predetermined duration or time or until the button is depressed. Alternatively, the LED may blink and the alarm may activate at preset intervals and duration if the patient did not press the button indicating that the indicated medication was taken. Depressing the button will then reset the timer for another 24 hours. If the person is taking a medication that requires twice daily usage then the initial depression of the button will cause the notification device to activate 12 hours later. If the person does not acknowledge the notification device by depressing the button at that time the device will sound and/or LED will activate every hour for a predetermined time and duration or until the button is depressed. Once the button is depressed the timer will reset for an additional 12 hours. If the person is taking a medication that requires three times per day usage then the initial depression of the button will cause the notification device to activate 8 hours later. The notification device will be activated for a predetermined time or until the button is depressed. Once the button is depressed the timer will reset for an additional 8 hours. If the person is taking a medication that requires four times per day usage then the initial depression of the button will cause the notification device to activate 6 hours later. The notification device will be activated for a predetermined time or until the button is depressed. Depressing the button will reset the timer for an additional 6 hours. The same concept will apply to medications taken on other schedules. If the patient presses the button before the correct time the beep, LED or other notification device will not activate indicating that the action is not acceptable.

The above embodiments may be modified such that depressing the button within, as an example, 30 minutes before the scheduled time will cause that additional time to be added to the next time the timer is scheduled to activate. The device will beep or another notification device will activate acknowledging that this is an accepted action. If the patient attempts to take a medication too early, i.e., two hours after the last dose of a medication taken four times a day the device will not beep and/or the LED will not activate, indicating that the action is unacceptable. But, if a medication is to be taken 4 times per day and a patient takes the last pill for the day at 11:30 PM instead of the scheduled time of 12 AM the 30 minutes are added to the next dose, which will now be 6 am. The duration of "acceptable actions" may be programmable or preset.

Alternatively, a separate LED, of another color, may be provided that will illuminate when the patient presses the button before the recommended time to take the medication. An option allowing the patient to program the timer may be provided. The battery powering the device may or may not be replaceable, or rechargeable.

Figure 8:
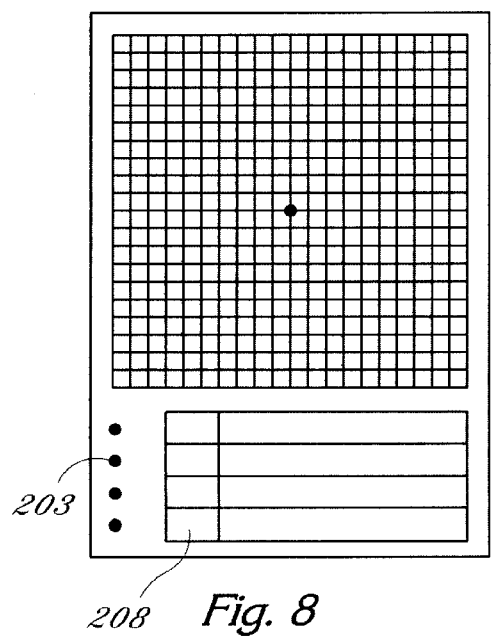
FIG. 8. Illustrates a front view of the eighth embodiment of the eye self-test device in which a digital display is provided.

FIG. 8 illustrates an eighth embodiment of the self-test device wherein a digital readout (208) is provided on each line of the medication reminder. The readout may indicate the number of medication doses remaining to be taken that day and/or the number of medication doses already taken that day. The digital readout may also be made to flash or light up when a particular medication is scheduled to be taken. Alternatively, one button may be used for programming and for the patient to depress when taking the indicated medication.

Figure 9:
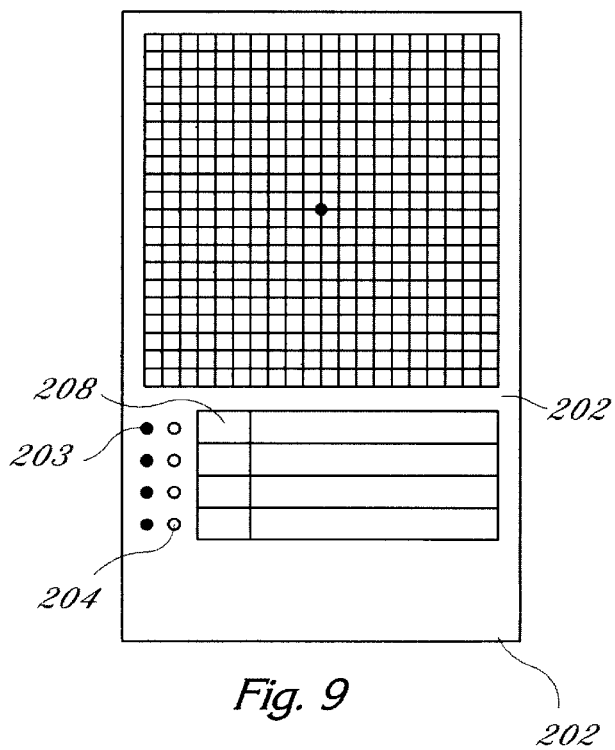
FIG. 9. Illustrates a front view of the ninth embodiment of the eye self-test device in which the alarms are programmable.

FIG. 9 illustrates a ninth embodiment of the self-test device wherein the timers are programmable by the patient, pharmacist or doctor such that the medications may be taken at particular times that may be required or are more convenient for the patient to take. A digital readout (208) and/or an LED (204) and alarm may be provided. Space for advertising or other messages may also be provided (202) on all the embodiments. One button may be provided for programming and for the patient to depress when taking the medication.

Figure 10:
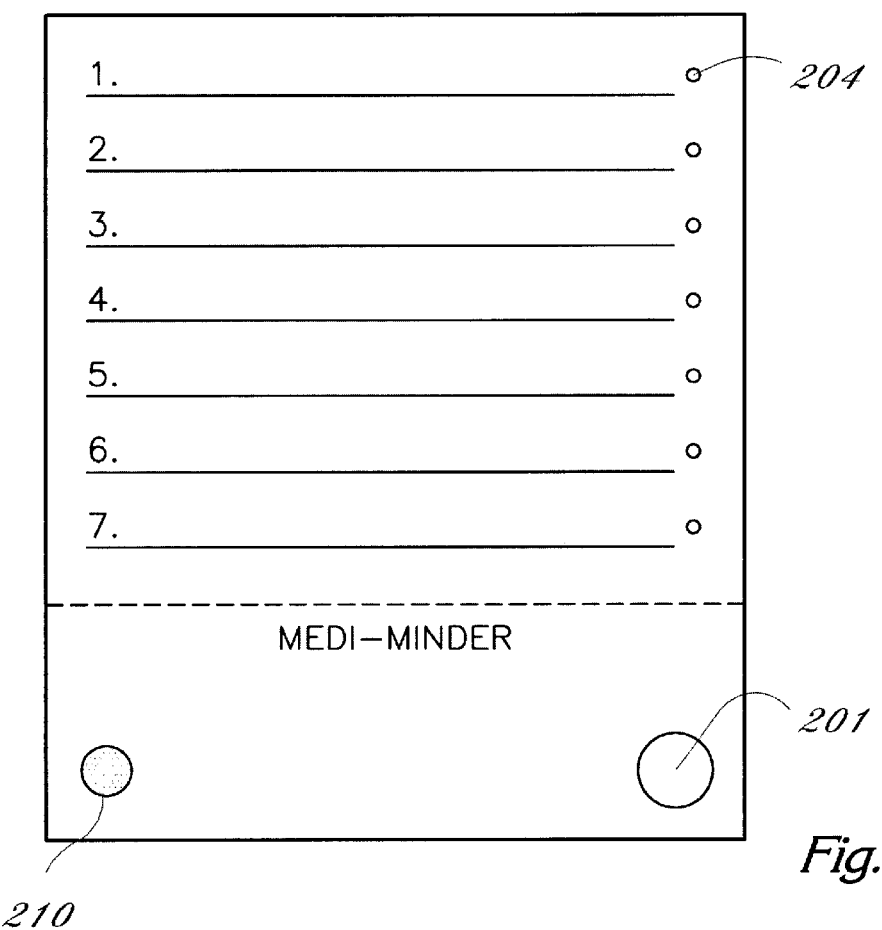
FIG. 10. Illustrates a front view of the tenth embodiment of the device which is used as a medication, event, or other type of reminder.
Figure 10A:
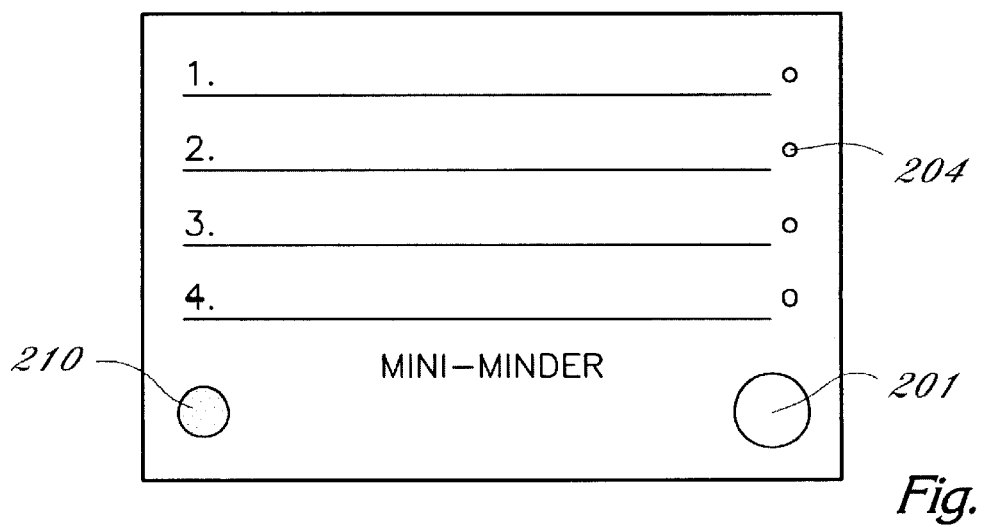

FIG. 10 illustrates a tenth embodiment of the device wherein the grid is replaced by an area allowing the writing of medications, dates or other events or occasions for which the device may be used as a reminder. A smaller, credit card sized version (FIG. 10A) is also illustrated. A speaker 210 can be provided to permit an audible noise to serve as the reminder. An illumination member, such as an LED (not shown), can also be provided in lieu of speaker 210 or in addition thereto.

It should also be recognized that the reminder embodiments of the present invention can be provided without the self-test grid.

In all cases, the size of this device is not limiting and while it may be placed on the refrigerator, bathroom mirror or another place of the patients choosing it is also expected that it may be carried in a persons pocket, pocketbook, briefcase, or worn on a belt, or other garment to remind the patient to test with the grid and/or take a medication or provide an event notification and such uses are also within the scope of the invention. It is also apparent to someone skilled in the art that other attention getting devices, i.e., clock, may be added and that various combinations of the above features as well as variations in the notification and programming sequence may be advantageous and are also within the scope of this invention.

In should also be understood that the term "medication" is not limited to prescription drugs, and includes any type of drug, herbs, vitamins, minerals, foods, liquids, etc. that the user wishes to be reminded about. The word "event" includes the taking of a "medication" or any other specific event that the user wishes to be reminded about.

The tests use conventional electrical and computer technology for programming and operational purposes, and are not limited to any one specific analog or digital embodiment. Furthermore, conventional software can be used for instructing the computer and microprocessor. Accordingly, any known electronic devices, chips, circuitry, components, hardware/software can be used to achieve the functions of the invention and are considered within the scope of the invention.

The instant invention has been shown and described herein in what is considered to be the most practical and preferred embodiment. It is recognized, however, that departures may be made from within the scope of the invention and that obvious modifications will occur to a person skilled in the art.

What is claimed is:

1. An eye self test comprising:

a housing member having an outer surface, at least a portion of the outer surface having a designated self examination testing area; and means for entering a test taking event interval period, said means for entering contained by said housing member.

2. The eye self test of claim 1 further including means for acknowledging that a user is performing a self test taking event, said means for acknowledging contained by said housing member; and means for indicating that said means for acknowledging has not been activated during an entered testing interval period.

3. The eye self test of claim 2 further including means for attaching said housing member to a surface.

4. The eye self test of claim 3 wherein said means for attaching is at least one magnet or adhesive associated with a back surface of said housing member.

5. The eye self test of claim 2 wherein said means for indicating is an audible sound.

6. The eye self test of claim 2 wherein said means for indicating is an illumination member.

7. The eye self test of claim 1 wherein said examination area includes an externally visible grid.

8. The eye self test of claim 1 wherein said testing interval period is one day, two days, three days or longer.

9. A self-contained event reminder comprising:

a body member having an area for identifying an event to be performed, said area including a digital printout of a numerical value representing a number of times the identified event is to be performed;

means for entering an interval period for the repeated performance of the event, said means for entering housed by said body member;

user triggered means for acknowledging that the event has been performed;

means for indicating to a user that said means for acknowledging has not been activated during an entered interval period.

10. The event reminder of claim 9 wherein said event is the taking of a medication and the numerical value corresponds to the number of times in an interval period that the medication is taken.

11. The event reminder of claim 10 wherein activating said means for acknowledging incrementally decreases said numerical value.

12. The event reminder of claim 9 wherein said means for indicating is an audible sound.

13. The event reminder of claim 9 wherein said means for indicating is an illumination member.

14. The event reminder of claim 9 further including means for attaching said body member to a surface, said means for attaching disposed on a back surface of said body member.

15. The self-contained event reminder of claim 9 wherein said body member is attached to the surface without modification to the surface.

16. The self contained event reminder of claim 9 wherein all data regarding the event is entered, stored and processed solely by said self-contained event reminder.

17. The self-contained event reminder of claim 9 further including a means for powering housed by said body member.

* * * * *